(12) United States Patent
Patel

(10) Patent No.: US 7,476,655 B2
(45) Date of Patent: Jan. 13, 2009

(54) MATERIALS AND METHODS FOR REGULATING BLOOD FLOW

(75) Inventor: Jawaharlal M. Patel, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 305 days.

(21) Appl. No.: 11/433,113

(22) Filed: May 12, 2006

(65) Prior Publication Data

US 2006/0258592 A1 Nov. 16, 2006

Related U.S. Application Data

(60) Provisional application No. 60/680,217, filed on May 12, 2005.

(51) Int. Cl.
*A61K 38/00* (2006.01)

(52) U.S. Cl. ...................................................... 514/12

(58) Field of Classification Search .................... 514/12
See application file for complete search history.

(56) References Cited

FOREIGN PATENT DOCUMENTS

WO WO 98/02555 A 1/1998

OTHER PUBLICATIONS

Chen, P. et al., "Characterization of the Roles of the 594-645 Region in Human Endothelial Nitric-oxide Synthase in Regulating Calmodulin Binding and Electron Transfer," *The Journal of Biological Chemistry*, Apr. 2000, pp. 13155-13163, vol. 275, No. 17.
Chen, S. et al., "Angiotensin IV-Mediated Pulmonary Artery Vasorelaxation is Due to Endothelial Intracellular Calcium Release," *Am. J. Physiol. Lung Cell Mol. Physiol.*, 2000, pp. L849-L856, vol. 279.
Farber, H. et al., "Pulmonary Arterial Hypertension," *N. Engl. J. Med.*, Oct. 2004, pp. 1655-1665, vol. 351, No. 16.
Galiè, N. et al., "Prostanoids for Pulmonary Arterial Hypertension," *Am. J. Respir. Med.*, 2003, pp. 123-137, vol. 2, No. 2.
Garcí-Cardenña, G. et al., "Dynamic Activation of Endothelial Nitric Oxide Synthase by Hsp90," *Nature.*, Apr. 1998, pp. 821-824, vol. 392.
Garcí-Cardenña, G. et al., "Endothelial Nitric Oxide Synthase is Regulated by Tyrosine Phosphorylation and Interacts with Caveolin-1," *J. Biol. Chem.*, Nov. 1996, pp. 27237-27240 vol. 271, No. 44.
Giaid, A. et al., "Reduced Expression of Endothelial Nitric Oxide Synthase in the Lungs of Patients with Pulmonary Hypertension," *N. Engl. J. Med.*, Jul. 1995, pp. 214-221, vol. 333, No. 4.
Hu, H. "Autoinhibitory domain fragment of endothelial NOS enhances pulmonary artery vasorelaxation by the NO-cGMP pathway," *Am. J. Physiol. Lung Cell Mol. Physiol.*, May 2004, pp. L1066-L1074, vol. 286, No. 5.
Mani, S. et al. "Nitric Oxide Mediates Sexual Behavior in Female Rats," *Proc. Natl. Acad. Sci.*, Jul. 1994, pp. 6468-6472, vol. 91, No. 14.
Marletta, M., "Nitric Oxide Synthase Structure and Mechanism," *J. Biol. Chem.*, Jun. 1993, pp. 12231-12234, vol. 268, No. 17.
Mehta, S., "Drug Therapy for Pulmonary Arterial Hypertension: What's on the Menu Today?" *Chest*, Dec. 2003, pp. 2045-2049, vol. 124, No. 6.
Michel, T. et al., "Nitric Oxide Synthases: Which, Where, How and Why?" *J. Clin. Invest.*, Nov. 1997, pp. 2146-2152, vol. 100, No. 9.
Newman, J. et al., "Pulmonary Arterial Hypertension: Future Directions, Report of a National Heart, Lung, and Blood Institute/Office of Rare Diseases Workshop," *Circulation*, 2004, pp. 2947-2952, vol. 109.
Patel, J. et al., "Increased Expression of Calreticulin is Linked to ANG IV-Mediated Activation of Lung Endothelial NOS," *Am. J. Physiol. Lung Cell Mol. Physiol.*, 1999, pp. 794-801, vol. 277.
Salerno, J. et al., "An Autoinhibitory Control Element Defines Calcium-regulated Isoforms of Nitric Oxide Synthase," *The Journal of Biological Chemistry*, Nov. 1997, pp. 29769-29777, vol. 272, No. 47.
Schütte, H. et al., "The PDE inhibitor Zaprinast Enhances NO-Mediated Protection against Vascular Leakage in Reperfused Lungs," *Am. J. Physiol. Lung Cell Mol. Physiol.*, 2000, pp. 496-502, vol. 279.

*Primary Examiner*—Maryam Monshipouri
(74) *Attorney, Agent, or Firm*—Saliwanchik, Lloyd & Saliwanchik

(57) ABSTRACT

The subject invention provides materials and methods useful in regulating blood flow. In a preferred embodiment, the subject invention provides peptides that are able to enhance nitric oxide (NO) activity and/or elevate cellular guanosine monophosphate (cGMP). Through these mechanisms, the subject invention can be used advantageously to effect vasorelaxation, thereby providing therapeutic benefit in a variety of contexts. In a specific embodiment the subject invention provides novel peptides that have been found to enhance the activity of endothelial cell nitric oxide synthase (eNOS). These peptides have also been found to reduce the cGMP-specific phosphodiesterase activity.

6 Claims, 9 Drawing Sheets

SEQUENCE LISTING

```
<160> NUMBER OF SEQ ID NOS: 3

<210> SEQ ID NO 1
<211> LENGTH: 15
<212> TYPE: PRT
<213> ORGANISM: Artificial Sequence
<220> FEATURE:
<223> OTHER INFORMATION: Peptide (P3) used according to the subject
      invention.

<400> SEQUENCE: 1

Lys Arg Phe Asn Ser Ile Ser Cys Ser Ser Trp Arg Arg Lys Arg
1               5                   10                  15

<210> SEQ ID NO 2
<211> LENGTH: 19
<212> TYPE: PRT
<213> ORGANISM: Artificial Sequence
<220> FEATURE:
<223> OTHER INFORMATION: Peptide (P4) used according to the subject
      invention.
```

-continued

```
<400> SEQUENCE: 2

Lys Lys Arg Phe Asn Ser Ile Ser Cys Ser Ser Trp Arg Arg Lys Arg
1               5                   10                  15

Lys Lys Arg

<210> SEQ ID NO 3
<211> LENGTH: 8
<212> TYPE: PRT
<213> ORGANISM: Artificial Sequence
<220> FEATURE:
<223> OTHER INFORMATION: Peptide (P6) used according to the subject
      invention.

<400> SEQUENCE: 3

Trp Arg Arg Lys Arg Lys Glu Ser
1               5
```

MATERIALS AND METHODS FOR REGULATING BLOOD FLOW

CROSS-REFERENCE TO RELATED APPLICATIONS

This application claims the benefit of U.S. Provisional Application Ser. No. 60/680,217, filed May 12, 2005, which is hereby incorporated by reference in its entirety.

GOVERNMENT SUPPORT

The subject matter of this application has been supported by research grants from the National Institutes of Health (National Heart, Lung and Blood Institute), Grant Numbers 1R01 HL67886 and 1R01 HL68666 and by the Department of Veterans Affairs, Grant No. 0001 (Merit Review). Accordingly, the government may have certain rights in this invention.

BACKGROUND OF THE INVENTION

The regulation of blood flow in the various tissues throughout the body is a complicated process involving many factors. Blood pressure is maintained by regulation of cardiac output and peripheral resistance at the arterioles, postcapillary venules, and heart. The kidney contributes to maintenance of blood pressure by regulating blood volume. Central control of blood pressure is integrated and regulated by diffuse neurons within a region of the medulla oblongata loosely called the vasomotor center. Hypoxia or carbon dioxide directly stimulates the vasomotor center. It also receives input from sensors within the walls of the large arteries. Output from the vasomotor center alters heart rate and vascular tone to return blood pressure to acceptable levels.

Tissues can regulate their own blood flow through autoregulation. Local factors such as decreased oxygen, increased carbon dioxide, or increased osmolarity relax arterioles and precapillary sphincters. Lactate and potassium ion concentrations also cause local vasodilation. Injury causes arteries and arterioles to constrict to limit blood loss. Temperature decreases cause vasoconstriction in localized areas as well.

Circulating or local hormonal factors can change the caliber of the arterioles. Histamine, atrial natriuretic peptide, epinephrine, kinins, nitric acid, and adenosine are all vasodilators. Vasoconstrictors include vasopressin, norepinephrine, angiotensin II, and serotonin. The action of any of many of these substances depends on the tissue and receptor compliment of the cells there.

The precise control of blood flow is critical to the proper function of organs and tissue throughout the body and can also play a role in behavior, learning, and memory. Blood flow through the pulmonary circulation is highly regulated. For example, the pulmonary endothelium regulates pulmonary blood flow and maintains a low vascular resistance by releasing vasoactive substances that control vasomotor tone, vascular patency, and normal vessel wall architecture.

Pulmonary hypertension (PH) is a condition of increased pulmonary vascular resistance and pulmonary arterial pressure that interferes with ventilation-perfusion relationships. PH typically is characterized by increased blood pressure (above 30 mm Hg systolic and 12 mm Hg diastolic) within the pulmonary circulation.

There are two subsets of pulmonary hypertension: primary (idiopathic or "unexplained") and secondary. The secondary form is the more prevalent. The most common causes of secondary pulmonary hypertension are heart disease and lung disease. Regardless of the root cause of the pulmonary hypertension, the vessels of the lungs undergo anatomic changes that contribute to the progression of pulmonary hypertension.

Nitric oxide is one compound that plays an important role in regulating pulmonary blood flow. However, it is a gas with no known storage mechanism, which diffuses freely across membranes and is extremely labile. Nitric oxide has a biological half-life on the order of seconds, and its production is tightly regulated.

Nitric oxide is produced by two classes of nitric oxide synthases (NOS). The constitutively expressed nitric oxide synthases exist as two isoforms: the endothelial nitric oxide synthase (eNOS) and the neuronal nitric oxide synthase, (nNOS). These isoforms are expressed in vascular endothelial cells, platelets, and in neural tissues such as the brain.

In blood vessels eNOS mediates endothelium dependent vasodilation in response to various mediators. Nitric oxide levels increase in response to shear stress, i.e., forces on the blood vessels in the direction of blood flow, and are the mediators of inflammation.

In the nervous system, the neuronal NOS isoform is localized to discrete populations of neurons in the cerebellum, olfactory bulb, hippocampus, corpus striatum, basal forebrain, and brain stem.

The second class of nitric oxide synthase, inducible nitric oxide synthase (iNOS), is expressed in macrophages, hepatocytes, and tumor cells. Steuhr et al., Adv. Enzymol. Relat. Areas Mol. Biol. 65:287-346 (1992); Lowenstein et al., Proc. Natl. Acad. Sci. (USA) 89:6711-6715 (1992). This form of NOS functions as a cytotoxic agent, and NO produced by inducible NOS targets tumor cells and pathogens.

All isoforms of NOS catalyze the conversion of L-arginine to L-citrulline with production of NO. In vascular smooth muscle cells and in platelets, NO activates soluble guanylate cyclase, which increases intracellular guanosine 3',5'-cyclic monophosphate (cGMP), thereby inducing vasorelaxation and inhibiting platelet aggregation.

Pulmonary arterial hypertension secondary to acquired heart disease begins with a disorder of the left ventricle that leads to pulmonary venous hypertension followed by pulmonary arterial hypertension. The pathobiology of PAH is complex. Vascular endothelial cell dysfunction appears to be a factor in the development of PAH as vascular endothelium-derived mediators including nitric oxide (NO) play a role in the regulation of vascular function through NO/cGMP-mediated vasorelaxation in the pulmonary circulation. Reduced expression of eNOS and/or diminished production of NO in the lungs of patients with pulmonary hypertension have been observed (Giaid A, and D. Saleh (1995) "Reduced expression of endothelial nitric oxide synthase in the lungs of patients with pulmonary hypertension" *N. Engl. J. Med.* 333:214-221). Vascular endothelial cells generate NO from the metabolism of L-arginine via an oxidative catabolic reaction mediated by eNOS (Michel T. and O. Feron (1997) "Nitric oxide synthases: Which, where, how, and why?" *J. Clin. Invest.* 100:2146-2152; Garcia-Cardena G, R. Fan, D. F. Stern, J. Liu, and W. C. Sessa (1996) "Endothelial cell nitric oxide synthase is regulated by tyrosinee phosphorylation and interacts with caveolin-1" *J. Biol. Chem.* 271:27237-27240), which activates soluble guanylate cyclase resulting in increased production of cGMP. Thus, physiologic action of NO is mediated through formation of cGMP or NO/cGMP signaling (Chen S, J. M. Patel and E. R. Block (2000) "Angiotensin IV-mediated pulmonary artery vasorelaxation is due to endothelial intracellular calcium release" *Am. J. Physiol. Lung Cell Mol. Physiol.* 279: L849-L856; Marletta, M. A. (1993) "Nitric oxide synthase structure and mechanism" *J.*

Biol. Chem. 268:12231-12234). Endothelial cell release of NO is enhanced by a number of receptor-mediated agonists including bradykinin, acetylcholine, histamine, angiotensin IV, and serotonin via signal transduction-mediated activation of eNOS (Chen, S., J. M. Patel and E. R. Block (2000) "Angiotensin IV-mediated pulmonary artery vasorelaxation is due to endothelial intracellular calcium release" *Am. J. Physiol. Lung Cell Mol. Physiol.* 279: L849-L856; and Davis M G, G. J. Fulton and P. O. Hagen (1995) "Clinical biology of nitric oxide" *Br. J. Surg.* 82:1598-1610.). The catalytic activity of eNOS is regulated by multiple post-transcriptional mechanisms involving a variety of factors including phosphorylation state, calcium mobilization, and protein:protein interaction (Patel, J. M. et al. (1999) "Increased expression of calreticulin is linked to Ang-IV-mediated activation of lung endothelial NOS" *Am. J. Physiol Lung Cell Mol. Physiol.* 277:L794-L801 and Garcia-Cardena G. et al. (1998) "Dynamic activation of endothelial nitric oxide synthase by HSP 90" *Nature* 392:821-824).

The cellular level cGMP is critical for the regulation of multiple functions including vasorelaxation. A family of enzymes known as phosphodiestreases (PDE) is known to control transient and sustained elevation of cellular cGMP levels through modulation of hydrolysis activity. PDE-5 is the predominant cGMP-hydrolyzing PDE isoform in pulmonary vasculature. Zaprinast, a cGMP-specific PDE inhibitor, can enhance vasorelaxation in pulmonary circulation (Schutte, H., M. Witzenrath, K. Mayer, N. Weissmann, A. Schell, S. Rosseau, W. Seeger, and F. Grimminger (2000) "The PDE inhibitor Zaprinast enhances NO-mediated protection against vascular leakage in reperfused lungs" *Am. J. Physiol. Lung Cell Mol. Physiol.* 279:L496-L502).

With regard to PDE inhibitors, there are several non-peptide therapeutic agents specific for inhibition of selective isoforms of PDE's, one of which is approved or used in human studies for the regulation of pulmonary vascular function in the US. Although Zaprinast is a selective inhibitor of PDE 5, a dominant isoform in the pulmonary vasculature endothelium, its pharmacologic effects have only been tested in an animal model. In addition, none of these agents are known to modulate cellular levels of cGMP through eNOS activation and NO production. Their physiologic action is exclusively based on reduced hydrolysis of cGMP.

Pulmonary arterial hypertension (PAH) is characterized by vascular obstruction and sustained elevation of pulmonary pressure or vasoconstriction. PAH is classified as primary (idiopathic) or secondary, associated with collagen vascular diseases.

Although the pathogenesis of PAH is not well understood, a number of intrinsic and extrinsic factors play a role in causing imbalance in the generation of vasodilators and vasoconstrictors in the circulation. This can lead to the development of histologic lesions including pulmonary arteriolar occlusion (Farber, H. W. and J. Loscalzo (2004) "Mechanism of Disease: Pulmonary arterial hypertension" *N. Engl. J. Med.* 351:1655-1665, 2004 and Newman, J. H., B. L. Fanburg, S. L. Archer et al. (2004) "Pulmonary arterial hypertension: future directions" *Circulation* 109:2947-2952).

At present, therapeutic approaches for treatment of PAH include various prostacyclin formulations (iloprost, treprostinil, beraprost), supplemental oxygen, anticoagulant (warfarin), calcium channel blockers, endothelin antagonists (sitaxsentan), supplemental nitric oxide (NO), and phosphodiesterase inhibitors (zaprinast, sildenafil) with limited success (Galie, N., A. Manes, and A. Branzi (2003) "Prostanoids for pulmonary arterial hypertension" *Am. J. Respir. Med.* 2:123-137; and Mehta, S. (2004) "Drug therapy for pulmonary arterial hypertension: what's on the menu today?" *Chest* 124:2045-2049).

There is a need in the art for new composition and methods to help regulate blood flow in order to address various pathological conditions as well as to improve cognitive function.

BRIEF SUMMARY

The subject invention provides materials and methods useful in enhancing nitric oxide (NO) activity and/or elevating cellular guanosine monophosphate (cGMP). Through these mechanisms, the subject invention can be used advantageously to effect, for example, vasorelaxation.

In a specific embodiment the subject invention provides three peptides, designated herein as P3, P4, and P6, which have been found to enhance the activity of endothelial cell nitric oxide synthase (eNOS). These peptides have also been found to reduce the activity of cGMP-specific phosphodiesterase activity.

These peptides can also be used to inhibit cyclic adenosine monophosphate (cAMP)-dependent PDE isoforms and associated functions. Because of their advantageous physiological properties, the peptides of the subject invention can be used as described herein to regulate blood flow and to treat various conditions including, for example, pulmonary hypertension, sexual dysfunction, cerebral ischemia, reduce platelet aggregation, and enhance memory and learning. Specifically exemplified herein is the use of the peptides of the subject invention for the treatment of pulmonary arterial hypertension.

A further aspect of the subject invention pertains to pharmaceutical compositions comprising the peptides of the subject invention as well as methods for their delivery.

BRIEF DESCRIPTION OF THE DRAWINGS

The file of this patent contains at least one drawing executed in color. Copies of this patent with color drawings(s) will be provided by the Patent and Trademark Office upon request and payment of the necessary fee.

BRIEF DESCRIPTION OF THE SEQUENCES

Figure 1:
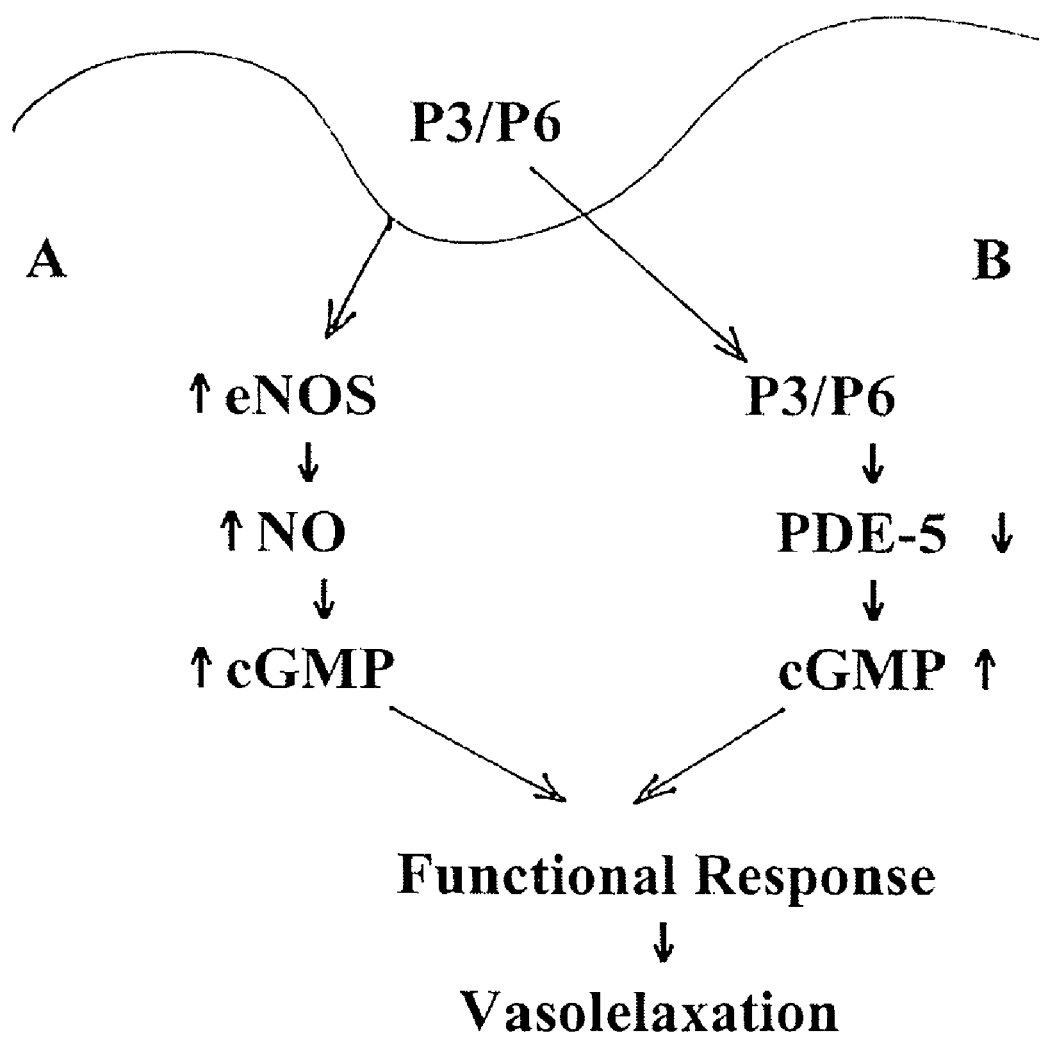
FIG. 1 depicts the mechanisms through the peptides of the subject invention that may exert their activity.

SEQ ID NO:1 is a synthetic peptide designated herein as P3: KRFNSISCSSWRRKR, which has been found to enhance the activity of endothelial cell nitric oxide synthase (eNOS).

SEQ ID NO:2 is a synthetic peptide designated herein as P4: KKRFNSISCSSWRRKRKKR, which has been found to enhance the activity of endothelial cell nitric oxide synthase (eNOS).

SEQ ID NO:3 is a synthetic peptide designated herein as P6: WRRKRKES, which has been found to enhance the activity of endothelial cell nitric oxide synthase (eNOS).

DETAILED DISCLOSURE

The subject invention provides materials and methods useful in regulating blood flow. In a preferred embodiment, the subject invention provides peptides that are able to enhance nitric oxide (NO) activity and/or elevate cellular guanosine monophosphate (cGMP). The peptides of the subject invention can also be used as inhibitors of phosphodiesterases (PDE). Through these mechanisms, the subject invention can be used advantageously to regulate blood in various tissues by, for example, effecting vasorelaxation, thereby providing therapeutic benefit in a variety of contexts.

In a specific embodiment the subject invention provides three peptides, designated herein as P3, P4, and P6, which have been found to enhance the activity of endothelial cell nitric oxide synthase (eNOS). These peptides have also been found to reduce the activity of cGMP-specific phosphodiesterase activity.

Because of their advantageous physiological properties, the peptides of the subject invention can be used as described herein to treat various conditions including, for example, pulmonary hypertension, sexual dysfunction, cerebral ischemia, and can reduce platelet aggregation, and enhance memory and learning. Specifically exemplified herein is the use of the peptides of the subject invention for the treatment of pulmonary arterial hypertension.

Furthermore through the inhibition of specific isoforms of PDE, the peptides of the subject invention can be used in various therapeutic methods. Specific therapeutic uses of the PDE inhibitors of the subject invention include the following:

PDE5=Vasodilation
PDE3/4=Bronchodilation and Anti-inflammatory
PDE4=Anti-inflammatory
PDE3=Cardiac effects In specific embodiments, the peptides of the subject invention can be used to regulate blood flow in the heart, brain, kidneys, lungs, and/or other organs.

A further aspect of the subject invention pertains to pharmaceutical compositions comprising the peptides of the subject invention.

The peptides specifically exemplified herein are as follows:

```
P3: KRFNSISCSSWRRKR;       (SEQ ID NO:1)

P4: KKRFNSISCSSWRRKRKKR;   (SEQ ID NO:2)
and

P6: WRRKRKES               (SEQ ID NO:3)
```

The peptides of the subject invention can be used as therapeutic agents in the regulation of eNOS activity, NO production, and NO/cGMP-mediated vasorelaxation as well as inhibition of PDE activity leading to reduced hydrolysis of cGMP. The net result of these activities is the maintenance of sustained cellular levels of cGMP and cGMP-mediated functions.

The peptides of the subject invention are particularly advantageous because they can regulate cellular cGMP levels in at least one of two distinct mechanisms shown in FIG. 1, namely: i) activation of eNOS, generation of NO and increased production of cGMP and ii) inhibition of PDE activity resulting in reduced hydrolysis of cGMP with net result of sustained increase of cellular cGMP level.

Subjects that may be treated by the present invention include any subject, human or animal, for which it is desired to regulate blood flow. While subjects treated by the present invention are primarily human subjects, the invention may also be carried out on other animal subjects such as dogs, cats, horses, etc. for veterinary purposes.

As discussed in more detail below, active compounds useful for effecting the aforesaid therapies may be administered by any suitable means, including oral, intraperitoneal, subcutaneous, intraarterial, intravenous, intramuscular, and intrathecal injection. Injection may be through a syringe, through a canula or catheter into a desired vessel or organ, etc. The compounds may be administered by inhalation into the airways, and particularly the alveoli, of the lungs, such as by the inhalation of respirable aerosol particles (e.g., 1 to 5 micron diameter particles) comprising the active compounds.

For a number of reasons, such as local treatment of lung diseases, replacement of injection therapy and for rapid onset of action, administering drugs to the lungs of a patient is advantageous. A number of different devices have been developed in order to deliver drugs to the lung; e.g. pressurized aerosols (pMDIs), nebulizers and dry powder inhalers (DPIs).

While inhalation of drugs already is well established for local treatment of lung diseases, the lung is also an appealing site for systemic delivery of drugs, as it offers a large surface area (about 100 m$^2$) for the absorption of the molecules across a thin epithelium thereby giving potential for rapid drug absorption.

Pharmaceutical formulations of the invention, which are discussed in more detail below, typically comprise an active compound and a pharmaceutically acceptable carrier. Any pharmaceutically acceptable carrier may be employed, such as sterile saline solution, sterile water, etc. The active compound is included in the pharmaceutically acceptable carrier in any suitable amount, such as between about 0.001, 0.005 or 0.01 percent by weight to about 10, 20 or 50 percent by weight.

Dosage of the active compound will depend upon the particular peptide, the route of administration, the particular disorder being treated, the age, weight, and condition of the subject, etc. Excipients that are added to the peptide formulations to increase their stability include buffers, sugars, surfactants, amino acids, polyethylene glycols, and polymers.

The peptides may be administered either directly as described above or through a vector intermediate that expresses the same in the subject. Thus vectors used to carry out the present invention are, in general, RNA virus or DNA virus vectors, such as lentivirus vectors, papovavirus vectors (e.g., SV40 vectors and polyoma vectors), adenovirus vectors and adeno-associated virus vectors. See generally T. Friedmann, Science 244, 1275 16 (June 1989). Examples of lentivirus vectors that may be used to carry out the present invention include Moloney Murine Leukemia Virus vectors, such as those described in U.S. Pat. No. 5,707,865 to Kohn. Any adenovirus vector can be used to carry out the present invention. See, e.g., U.S. Pat. No. 5,518,913, U.S. Pat. No. 5,670,488, U.S. Pat. No. 5,589,377; U.S. Pat. No. 5,616,326; U.S. Pat. No. 5,436,146; and U.S. Pat. No. 5,585,362. The adenovirus can be modified to alter or broaden the natural tropism thereof, as described in S. Woo, Adenovirus redirected, Nature Biotechnology 14, 1538 (November 1996). Any adeno-associated virus vector (or AAV vector) can also be used to carry out the present invention. See, e.g., U.S. Pat. No. 5,681,731; U.S. Pat. No. 5,677,158; U.S. Pat. No. 5,658,776; U.S. Pat. No. 5,658,776; U.S. Pat. No. 5,622,856; U.S. Pat. No. 5,604,090; U.S. Pat. No. 5,589,377; U.S. Pat. No. 5,587,308; U.S. Pat. No. 5,474,935; U.S. Pat. No. 5,436,146; U.S. Pat. No. 5,354,678; U.S. Pat. No. 5,252,479; U.S. Pat. No. 5,173,414; U.S. Pat. No. 5,139,941; and U.S. Pat. No. 4,797,368. The regulatory sequences, or the transcriptional and translational control sequences, in the vectors can be of any suitable source, so long as they effect expression of the heterologous nucleic acid in the target cells. For example, commonly used promoters are the LacZ promoter, and promoters derived from polyoma, Adenovirus 2, and Simian virus 40 (SV40). See, e.g., U.S. Pat. No. 4,599,308. Once prepared, the recombinant vector can be reproduced by (a) propagating the vector in a cell culture, the cell culture comprising cells that permit the growth and reproduction of the vector therein; and then (b) collecting the recombinant vector from the cell culture, all in accordance with known techniques. The viral vectors collected from the culture may be separated from the culture medium in accordance with known techniques, and combined with a suitable pharmaceutical carrier for administration to a subject. Such pharmaceutical carriers include, but are not limited to, sterile pyrogen-free water or sterile pyrogen-free saline solution. If desired, the vectors may be packaged in liposomes for administration, in accordance with known techniques. See, e.g., U.S. Pat. No. 6,875,749.

Formulations and Administration

The pharmaceutical compositions of the invention encompass liquid compositions and dried forms thereof. For purposes of the present invention, the term "liquid" with regard to pharmaceutical compositions or formulations includes the term "aqueous", and includes liquid formulations that are frozen. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). The term "lyophilize" refers to rapid freeze drying under reduced pressure of a plurality of vials, each containing a unit dose of the peptide formulation of the present invention therein. Lyophilizers, which perform the above described lyophilization, are commercially available and readily operable by those skilled in the art. In one embodiment of the present invention, the liquid composition is prepared as a lyophilized composition.

In one embodiment of the invention, the pharmaceutical compositions can be prepared in a form that is suitable for pulmonary delivery and administering the preparation to the subject via pulmonary inhalation. By "pulmonary inhalation" is intended the pharmaceutical composition is directly administered to the lung by delivering the composition in an aerosol or other suitable preparation from a delivery device into the oral cavity of the subject as the subject inhales through the oral cavity. By "aerosol" is intended a suspension of solid or liquid particles in flowing air or other physiologically acceptable gas stream. Other suitable preparations include, but are not limited to, mist, vapor, or spray preparations so long as the particles comprising the peptide composition are delivered in a size range consistent with that described for a dry powder form of the pharmaceutical composition as defined below. Pulmonary inhalation can also be accomplished by other suitable methods known to those skilled in the art. These include liquid instillation using a suitable device or other such methods. Pulmonary inhalation results in deposition of the inhaled protein composition in the alveoli of the subject's lungs. Once deposited, the protein may be absorbed, passively or actively, across the alveoli epithelium and capillary epithelium layers into the bloodstream.

Pulmonary administration of a peptide requires dispensing of the biologically active substance from a delivery device into a subject's oral cavity during inhalation. For purposes of the present invention, pharmaceutical compositions comprising the peptides can be administered via inhalation of an aerosol or other suitable preparation that is obtained from an aqueous or nonaqueous solution or suspension form, or a solid or dry powder form of the pharmaceutical composition, depending upon the delivery device used. Such delivery devices are well known in the art and include, but are not limited to, nebulizers, metered-dose inhalers, and dry powder inhalers, or any other appropriate delivery mechanisms that allow for dispensing of a pharmaceutical composition as an aqueous or nonaqueous solution or suspension or as a solid or dry powder form. When used in the context of pharmaceutical compositions suitable for pulmonary delivery, these terms have the following intended meaning. By "aqueous" is intended a composition prepared with, containing, or dissolved in water, including mixtures wherein water is the predominating substance in the mixture. By "nonaqueous" is intended a composition prepared with, containing, or dissolved in a substance other than water or mixtures wherein water is not the predominating substance in the mixture. By "solution" is intended a homogeneous preparation of two or more substances, which may be solids, liquids, gases, or intercombinations thereof. By "suspension" is intended a mixture of substances such that one or more insoluble substances are homogeneously dispersed in another predominating substance.

For purposes of the present invention, the terms "solid" and "dry powder" are used interchangeably with reference to the pharmaceutical compositions. By "solid" or "dry powder" form of a pharmaceutical composition is intended the composition has been dried to a finely divided powder having a moisture content below about 10% by weight, usually below about 5% by weight, and preferably below about 3% by weight. This dry powder form of the composition consists of particles comprising the peptides of the subject invention. Preferred particle sizes are less than about 10.0 μm mean diameter, more preferably less than about 7.0 μm, even more preferably about less than about 6.0 μm, even more preferably in the range of 0.1 to 5.0 μm, most preferably in the range of about 1.0 to about 5.0 μm mean diameter.

Thus, a liquid pharmaceutical composition comprising the peptides or variants thereof which is intended for pulmonary delivery can either be used as a liquid solution or suspension in the delivery device or first be processed into a dry powder form using lyophilization or spray-drying techniques well known in the art. Where a liquid solution or suspension is used in the delivery device, a nebulizer, a metered dose inhaler, or other suitable delivery device delivers, in a single or multiple fractional dose, by pulmonary inhalation a pharmaceutically effective amount of the composition to the subject's lungs as droplets having the same particle size range noted above for the dry powder form. By "pharmaceutically effective amount" is intended an amount that is useful in the treatment or prevention of a disease or condition responsive to the subject peptides. The liquid solution or suspension of the composition may be used with physiologically appropriate stabilizing agents, excipients, viscosity modifiers, bulking agents, surfactants, or combinations thereof, known to those of skill in the art, so long as they don't compromise the distinguishing characteristics of the peptide compositions of the invention.

Where the liquid pharmaceutical composition is lyophilized prior to use in pulmonary delivery, the lyophilized composition is milled to obtain the finely divided dry powder consisting of particles within the desired size range noted above. Where spray-drying is used to obtain a dry powder form of the liquid pharmaceutical composition, the process is carried out under conditions that result in a substantially amorphous finely divided dry powder consisting of particles within the desired size range noted above. For methods of preparing dry powder forms of pharmaceutical compositions, see, for example, WO 96/32149; WO 97/41833; WO 98/29096; and U.S. Pat. Nos. 5,976,574; 5,985,248; 6,001,336; and 6,875,749 herein incorporated by reference.

Where the dry powder form of the pharmaceutical composition is to be prepared and dispensed as an aqueous or nonaqueous solution or suspension, a metered-dose inhaler, or other appropriate delivery device is used.

A pharmaceutically effective amount of the dry powder form of the composition is administered in an aerosol or other preparation suitable for pulmonary inhalation. The amount of dry powder form of the composition placed within the delivery device is sufficient to allow for delivery of a pharmaceutically effective amount of the composition to the subject by inhalation. The delivery device delivers, in a single or multiple fractional dose, by pulmonary inhalation a pharmaceutically effective amount of the composition to the subject's lungs. The aerosol propellant may be any conventional material employed for this purpose. A surfactant may be added to the pharmaceutical composition to reduce adhesion of the protein-containing dry powder to the walls of the delivery device from which the aerosol is dispensed. Suitable surfactants for this intended use include, but are not limited to, sorbitan trioleate, soya lecithin, and oleic acid. Devices suitable for pulmonary delivery of a dry powder form of a protein composition as a nonaqueous suspension are commercially available. Examples of such devices include the Ventolin metered-dose inhaler (Glaxo Inc., Research Triangle Park, N.C.) and the Intal Inhaler (Fisons, Corp., Bedford, Mass.). See also the aerosol delivery devices described in U.S. Pat. Nos. 5,522,378; 5,775,320; 5,934,272; and 5,960,792 herein incorporated by reference.

Where the solid or dry powder form of the pharmaceutical composition is to be delivered as a dry powder form, a dry powder inhaler or other appropriate delivery device is preferably used. Examples of commercially available dry powder inhalers suitable for use in accordance with the methods herein include the Spinhaler powder inhaler (Fisons Corp., Bedford, Mass.) and the Ventolin Rotahaler (Glaxo, Inc., Research Triangle Park, N.C.). See also the dry powder delivery devices described in WO 93/00951, WO 96/09085, WO 96/32152, and U.S. Pat. Nos. 5,458,135, 5,785,049, and 5,993,783, herein incorporated by reference.

The dry powder form of the pharmaceutical composition comprising the peptide or active variant thereof can be reconstituted to an aqueous solution for subsequent delivery as an aqueous solution aerosol using a nebulizer, a metered dose inhaler, or other suitable delivery device. Nebulizers are commercially available and include, for example, the Ultravent nebulizer (Mallinckrodt Inc., St. Louis, Mo.) and the Acorn II nebulizer (Marquest Medical Products, Englewood, Colo.). See also the nebulizer described in WO 93/00951, and the device for delivering aerosolized aqueous formulations described in U.S. Pat. No. 5,544,646; herein incorporated by reference.

The pharmaceutical compositions of the present invention can be "stabilized" compositions. The pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject.

The stabilized pharmaceutical formulations of the invention comprise the exemplified peptides and variants thereof. Variants have amino acid sequences that are the same as, similar to, or substantially similar to the sequence shown in SEQ ID NOs:1-3. Fragments or truncated forms that retain their activity are also encompassed.

Variants with one or more mutations that improve, for example, their pharmaceutical utility are also encompassed by the present invention.

The skilled artisan will appreciate that changes can be introduced by mutation into the nucleotide sequences encoding the peptides, thereby leading to changes in the amino acid sequence, without altering the biological activity of the interferon. Thus, an isolated nucleic acid molecule encoding a variant having a sequence that differs from the amino acid sequence for the peptide can be created by introducing one or more nucleotide substitutions, additions, or deletions into the corresponding nucleotide sequence, such that one or more amino acid substitutions, additions or deletions are introduced into the encoded peptide. Mutations can be introduced by standard techniques. Such variants are also encompassed by the present invention.

For example, conservative amino acid substitutions may be made at one or more nonessential amino acid residues. A "nonessential" amino acid residue is a residue that can be altered from the sequence without altering its biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine), and aromatic side chains (e.g., tyrosine, phenylalanine, tryptophan, histidine).

Biologically active variants will generally have at least 80%, more preferably about 90% to about 95% or more, and most preferably about 96% to about 99% or more amino acid sequence identity to the amino acid sequence that serves as the basis for comparison. By "sequence identity" is intended the same amino acid residues are found within the variant polypeptide and the polypeptide molecule that serves as a reference when a specified, contiguous segment of the amino acid sequence of the variant is aligned and compared to the amino acid sequence of the reference molecule.

Thus, the determination of percent identity between any two sequences can be accomplished using a mathematical algorithm. One preferred non-limiting example of a mathematical algorithm utilized for the comparison of sequences is the algorithm of Myers and Miller (1988) Comput. Appl. Biosci. 4:11-7.

Biologically active variants encompassed by the invention also include peptides that have been covalently linked with, for example, polyethylene glycol (PEG) or albumin. These covalent hybrid molecules possess certain desirable pharmaceutical properties such as an extended serum half-life after administration to a patient. Methods for creating PEG adducts involve chemical modification of monomethoxypolyethylene glycol to create an activated compound that will react with the peptides. Methods for making and using PEG-linked polypeptides are described, for example in Delgado et al. (1992) Crit. Rev. Ther. Drug, Carrier Syst. 9:249-304. Methods for creating albumin fusion polypeptides involve fusion of the coding sequences for the polypeptide of interest and albumin and are described in U.S. Pat. No. 5,876,969, herein incorporated by reference.

Biologically active variants of peptides encompassed by the invention should retain the relevant activities, particularly the ability to enhance eNOS activity. In some embodiments the variant retains at least about 25%, about 50%, about 75%, about 85%, about 90%, about 95%, about 98%, about 99% or more of the biological activity of the polypeptides whose amino acid sequences are given in SEQ ID NOs: 1-3. Variants whose activity is increased in comparison with the activity of the polypeptides shown in SEQ ID NOs: 1-3 are also encompassed.

The formulations of the invention can be administered to any animal species including, but not limited to, avian, canine, bovine, porcine, equine, and human. Preferably, the subject is a mammalian species.

In some embodiments of the present invention, the peptide is recombinantly produced. The peptides can be produced by culturing a host cell transformed with an expression vector comprising a nucleotide sequence that encodes a peptide. The host cell is one that can transcribe the nucleotide sequence and produce the desired protein, and can be prokaryotic (for example, E. coli) or eukaryotic (for example a yeast, insect, or mammalian cell). Examples of recombinant production are given in Mantei et al. (1982) Nature 297:128; Ohno et al. (1982) Nucleic Acids Res. 10:967; Smith et al. (1983) Mol. Cell. Biol. 3:2156, and U.S. Pat. Nos. 4,462,940, 5,702,699, and 5,814,485; herein incorporated by reference. Alternatively, the peptide can be produced by a transgenic animal or plant that has been genetically engineered to express the protein of interest in accordance with methods known in the art.

Alternatively, the peptides can be synthesized chemically, by any of several techniques that are known to those skilled in the peptide art. See, for example, Li et al. (1983) Proc. Natl. Acad. Sci. USA 80:2216-2220, Steward and Young (1984) Solid Phase Peptide Synthesis (Pierce Chemical Company, Rockford, Ill.), and Baraney and Merrifield (1980) The Peptides: Analysis, Synthesis, Biology, ed. Gross and Meinhofer, Vol. 2 (Academic Press, New York, 1980), pp. 3-254, discussing solid-phase peptide synthesis techniques; and Bodansky (1984) Principles of Peptide Synthesis (Springer-Verlag, Berlin) and Gross and Meinhofer, eds. (1980) The Peptides: Analysis, Synthesis, Biology, Vol. 1 (Academic Press, New York), discussing classical solution synthesis.

Recombinantly produced peptides for use in preparing pharmaceutical compositions of the invention can be recovered and purified using any method known to one of skill in the art. Such methods include those disclosed in U.S. Pat. Nos. 4,462,940 and 5,702,699, herein incorporated by reference.

Compositions encompassed by the invention may have as little as about 0.01 mg/ml peptide and as much as about 20.0 mg/ml peptide (weight/volume). In various embodiments, the peptide is present at a concentration of about 0.01 mg/ml to about 20.0 mg/ml, about 0.015 mg/ml to about 12.5 mg/ml, about 0.025 mg/ml to about 10.0 mg/ml, about 0.05 mg/ml to about 8.0 mg/ml, about 0.075 mg/ml to about 6.0 mg/ml, about 0.1 mg/ml to about 4.0 mg/ml, about 0.125 mg/ml to about 2.0 mg/ml, about 0.175 mg/ml to about 1.0 mg/ml, about 0.2 mg/ml to about 0.5 mg/ml, about 0.225 mg/ml to about 0.3 mg/ml, and about 0.25 mg/ml.

In some embodiments, the formulations of the invention comprise a pharmaceutically acceptable carrier. By "pharmaceutically acceptable carrier" is intended a carrier that is conventionally used in the art to facilitate the storage, administration, and/or the healing effect of the therapeutic ingredients. A carrier may also reduce any undesirable side effects of the peptide. A suitable carrier should be stable, i.e., incapable of reacting with other ingredients in the formulation. It should not produce significant local or systemic adverse effects in recipients at the dosages and concentrations employed for treatment. Such carriers are generally known in the art. Suitable carriers for this invention are those conventionally used large stable macromolecules such as gelatin, collagen, polysaccharide, monosaccharides, polyvinyl-pyrrolidone, polylactic acid, polyglycolic acid, polymeric amino acids, fixed oils, ethyl oleate, liposomes, glucose, lactose, mannose, dextrose, dextran, cellulose, sorbitol, polyethylene glycol (PEG), and the like. Slow-release carriers, such as hyaluronic acid, may also be suitable. See particularly Prisell et al. (1992) Int. J. Pharmaceu. 85:51-56, and U.S. Pat. No. 5,166,331.

The pharmaceutical composition may additionally comprise a solubilizing agent or solubility enhancer that contributes to the peptide's solubility. Examples of such solubility enhancers include the amino acid arginine, as well as amino acid analogues of arginine that retain the ability to enhance solubility. Such analogues include, without limitation, dipeptides and tripeptides that contain arginine. Additional suitable solubilizing agents are discussed in U.S. Pat. Nos. 4,816,440; 4,894,330; 5,004,605; 5,183,746; 5,643,566; and in Wang et al. (1980) J. Parenteral Drug Assoc. 34:452-462; herein incorporated by reference.

Other stabilizing agents, such as ethylenediaminetetracetic acid (EDTA) or one of its salts such as disodium EDTA, can be added to further enhance the stability of the liquid pharmaceutical compositions. Other suitable stabilizing agents include non-ionic surfactants, including polyoxyethylene sorbitol esters such as polysorbate 80 (Tween 80) and polysorbate 20 (Tween 20); polyoxypropylene-polyoxyethylene esters such as Pluronic F68 and Pluronic F127; polyoxyethylene alcohols such as Brij 35; simethicone; polyethylene glycol such as PEG400; lysophosphatidylcholine; and polyoxyethylene-p-t-octylphenol such as Triton X-100. Classic stabilization of pharmaceuticals by surfactants is described, for example, in Levine et al. (1991) J. Parenteral Sci. Technol. 45(3):160-165, herein incorporated by reference.

By "pharmaceutically effective amount" is intended an amount that is useful in the treatment or prevention of a disease or condition. Typical routes of administration include, but are not limited to, oral administration, nasal delivery, pulmonary delivery, and parenteral administration, including transdermal, intravenous, intramuscular, subcutaneous, intraarterial, and intraperitoneal injection or infusion. In one such embodiment, the administration is by injection, preferably subcutaneous injection. Injectable forms of the compositions of the invention include, but are not limited to, solutions, suspensions, and emulsions. Typically, a therapeutically effective amount of the peptide comprises about 0.01 µg/kg to about 5 mg/kg of the composition, preferably about 0.05 µg/kg to about 1000 µg/kg, more preferably about 0.1 µg/kg to about 500 µg/kg, even more preferably still about 0.5 µg/kg to about 30 µg/kg.

The stabilized pharmaceutical composition may be sterilized by membrane filtration and is stored in unit-dose or multi-dose containers such as sealed vials or ampules. Additional methods for formulating a pharmaceutical composition generally known in the art may be used to further enhance storage stability of the pharmaceutical compositions disclosed herein provided they do not adversely affect the beneficial effects of the stabilizing agents as disclosed herein. A thorough discussion of formulation and selection of pharmaceutically acceptable carriers, stabilizers, etc. can be found in *Remington's Pharmaceutical Sciences* (1990) (18th ed., Mack Publishing Company, Eaton, Pa.), herein incorporated by reference.

Following are examples, which illustrate procedures for practicing the invention. These examples should not be construed as limiting. All percentages are by weight and all solvent mixture proportions are by volume unless otherwise noted.

EXAMPLE 1

Effects of Peptides on eNOS

The effects of the synthetic peptides (P3, P4, and P6) of the subject invention on the catalytic activity of eNOS were examined using a cultured pulmonary artery endothelial cell (PAEC) model.

PAEC monolayers were incubated in RPMI 1640 medium with or without (control) the presence of varying concentrations of P3, P4, or P6 at 37° C. for 1 hr. After incubation, the catalytic activity of eNOS was determined as previously described by monitoring formation of [3H]-citrulline from [3H]-L-arginine (Chen, S., J. M. Patel and E. R. Block ER (2000) "Angiotensin IV-mediated pulmonary artery vasorelaxation is due to endothelial intracellular calcium release" *Am. J. Physiol. Lung Cell Mol. Physiol.* 279:L849-L856; and Patel, J. M., Y. D. Li, J. L. Zhang et al. (1999) "Increased expression of calreticulin is linked to Ang-IV-mediated activation of lung endothelial NOS" *Am. J. Physiol Lung Cell Mol. Physiol.* 277:L794-L801).

Figure 2:
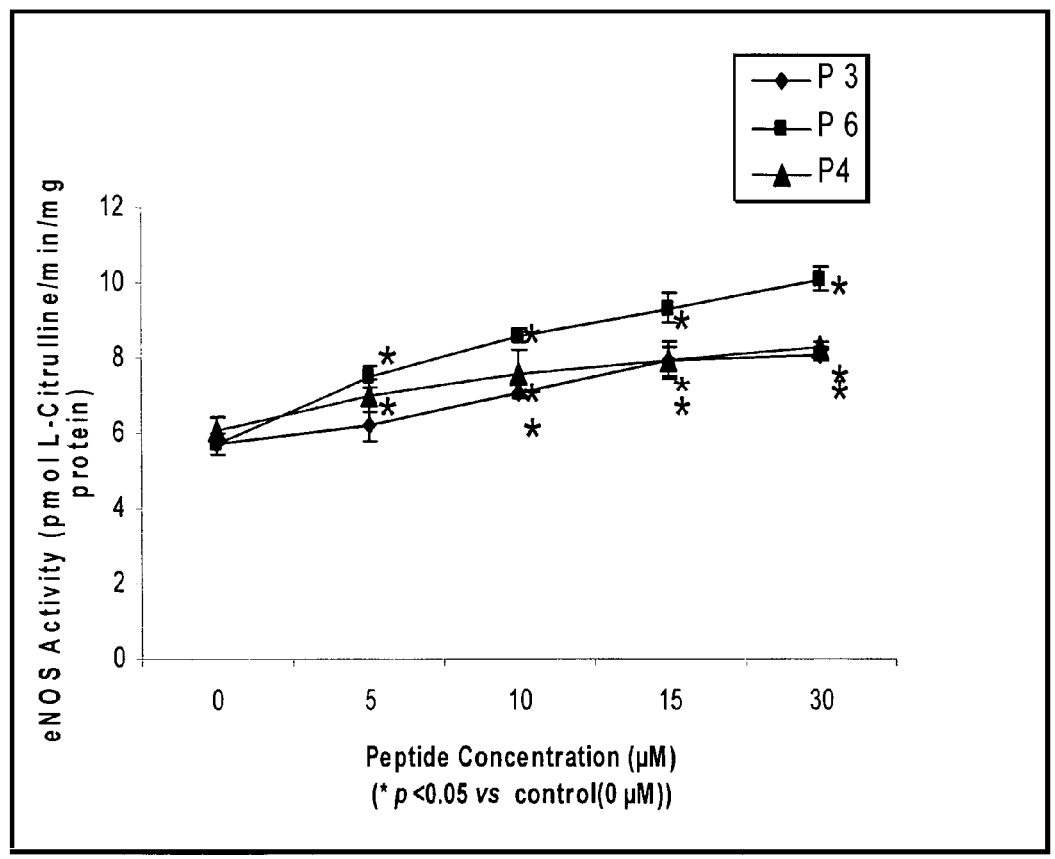
FIG. 2 shows the ability of the peptides of the subject invention to enhance eNOS activity.

As shown in FIG. 2, the catalytic activity of eNOS was significantly enhanced in a dose-dependent manner in cells stimulated P3, P4, and P6 compared to control.

EXAMPLE 2

Modulation of cGMP-Specific PDE Activity

The synthetic peptides were evaluated to asses any association with modulation of cGMP-specific PDE activity in PAEC.

Cell monolayers were incubated in RPMI 1640 medium with or without (control) the presence of 10 µM each of P3, P4, P6 or Zaprinast for 1 hr at 37° C. After incubation, cells were washed, homogenized, and supernatant were collected by centrifugation at 15,000×g for 15 min at 4° C. PDE activity in the supernatant were measured by monitoring hydrolysis of 3H-cGMP as previously described (16).

Figure 3:
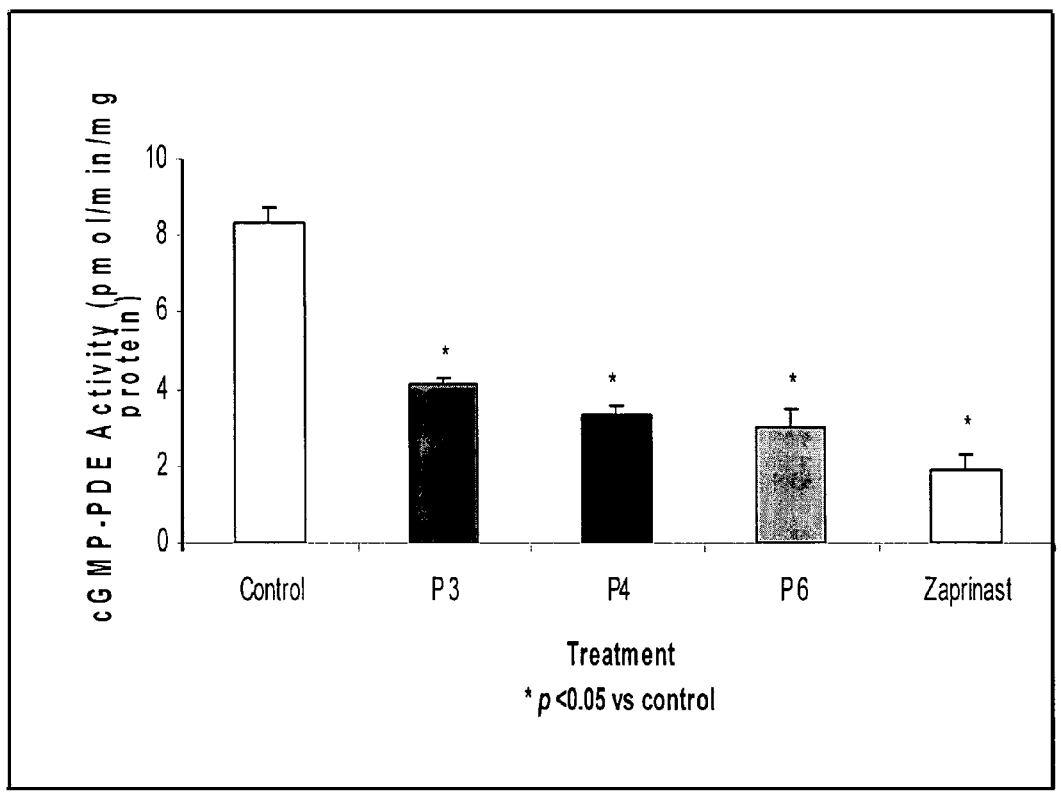
FIG. 3 shows the inhibition of cGMP-dependent activity with the peptides of the subject invention.

As shown in FIG. 3, cGMP-specific catalytic activity of PDE was significantly reduced by P3, P4, and P6 compared to control. The loss PDE activity by P3, P4, and P6 was comparable to that by the known inhibitor of PDE, Zaprinast.

The results indicate that inhibition of PDE activity can result in diminished hydrolysis of cGMP resulting in increased cellular levels of cGMP. Furthermore, these data in conjunction with the effect of these peptides on eNOS activity, suggest that sustained levels of cellular cGMP can be achieved by both the enhanced production of NO via activation of eNOS as well as decrease hydrolysis of cGMP via PDE inhibition by these novel peptides.

EXAMPLE 3

Vasodilation Effect in Hypoxic Lungs

Specific pathogen-free female C57BL/6J mice (30-35 g body weight) were anesthetized with pentobarbital (60 mg/kg, ip), and the lungs were excised from the thorax, ventilated with air (control) or with 0% oxygen for 1 hour at 60 breaths/min with a SAR-830 series small animal ventilator at a tidal volume of 0.6-0.8 ml/100 g body weight. After development of hypoxic vasoconstriction, vasodilator response was monitored by addition of 15 µM each of P3, P4, P6 or zaprinast with or without the presence of nitric oxide synthase inhibitor (L-NAME, 100 µM). The vasodilatory response was continuously monitored as previously described (Hu et al. (2004) *Am. J. Physiol. Lung Cell Mol. Physiol.* 286:L1066-L1074).

Figure 4:
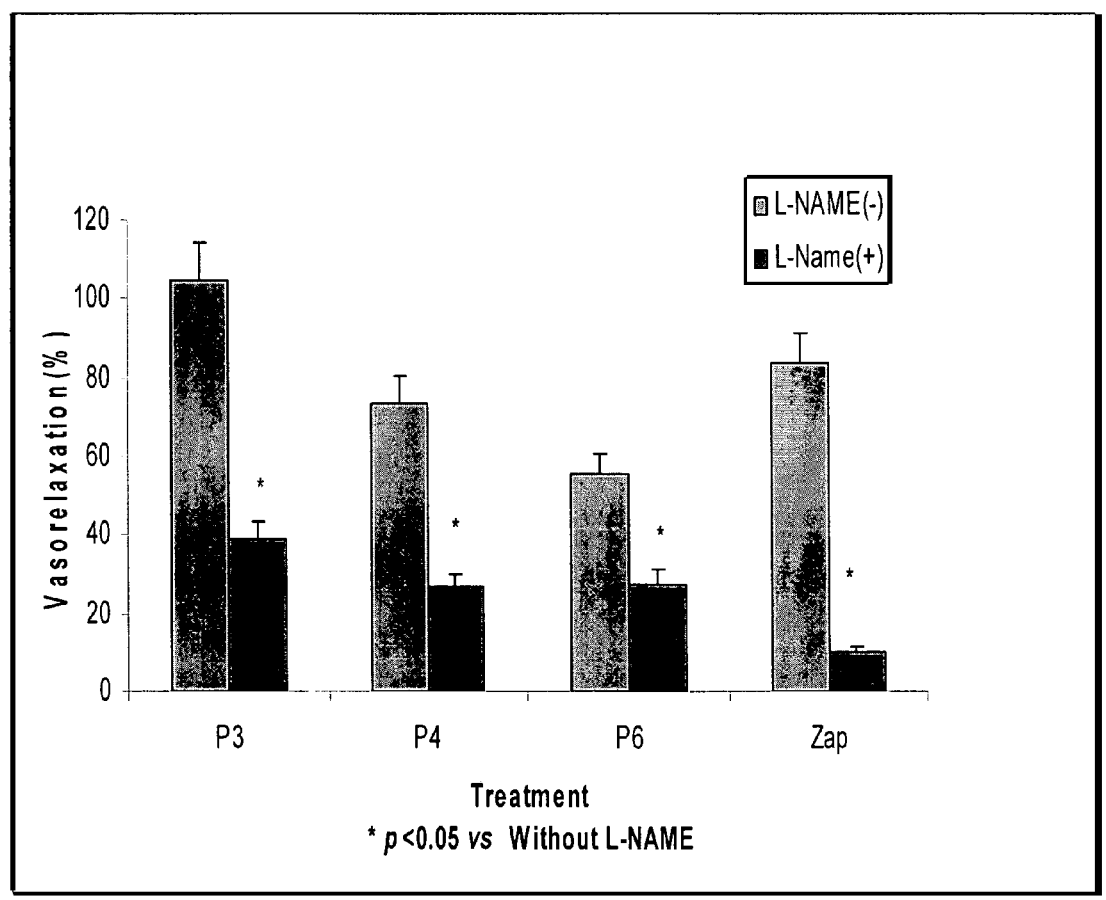
FIG. 4 shows peptide and zaprinase-induced vasorelaxtion of hypoxic mice lungs with or without nitric oxide synthase inhibitor L-NAME.
Figure 5:
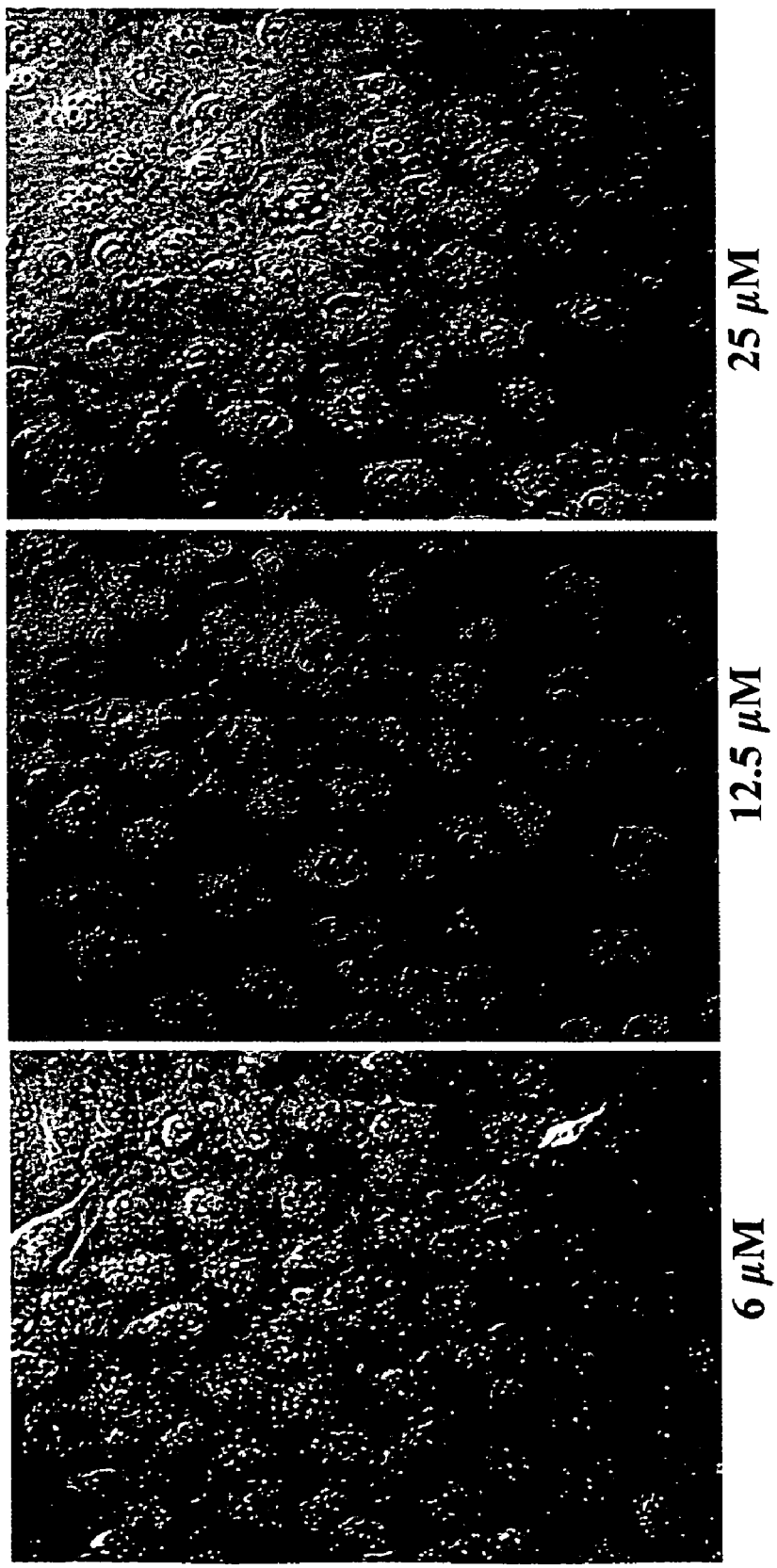
FIG. 5 shows inhibition of cGMP-phosphodiesterase (PDE) activity by peptides (P3,P4,P6) and zaprinast.

The results are shown in FIG. 4. Also, FIG. 5 shows internalization of FITC-labeled P3 in lung endothelial cells.

EXAMPLE 4

Hypoxic Lungs/in Situ Lung Perfusion

The following experimental evidence confirms P3-Mediated response using in situ rat models of hypoxic pulmonary hypertension.

Specific pathogen-free Sprague Dawley rats (200-250 g body weight) were anesthetized with pentobarbital (60 mg/kg, ip). After confirmation of deep anesthesia, the trachea was cannulated with an 18-G blunt-tipped catheter and ventilated (SAR-830/p small animal ventilator, CWE, Ardmoore, Pa.) at a tidal volume of 2.5 ml/min with warm humidified 21% $O_2$/5% $CO_2$/74% N2 at 60 breaths/min with peak inspiratory and expiratory pressures of 9 cm and 3 cm $H_2O$, respectively. A thoracotomy was performed and 100 units heparin injected into the right ventricle (RV). PE-90 polyethylene tubing connected to a Cook Double Lumen Central Venous Catheter (Cook Critical Care, Bloomington, Ind.) was placed in the left atrium through the left vetricle and tied in place. After placement of another PE-90 polyethylene tube connected with a double lumen catheter in the main pulmonary artery (PA), the lung were ventilated with 21% $O_2$/5% $CO_2$/74% N2 (normoxic) at constant end-expiratory pressure of 20 cm $H_2O$ and perfused in situ in the open chest with RPMI 1640 without pH indicator containing 4% Ficoll at a constant flow of 2 ml/min. After 30 min, the ventilation mixture was changed to 2% $O_2$/5% $CO_2$/93% $N_2$ (hypoxic) for 30 min and change in PA pressure was continuously recorded using PO-NE-MAH-P3P Lung Perfusion System software (Gould Instrument System) and the perfusate samples were collected to determine level of NO release as previously reported (Hu et al. Am. J. Physiol. Lung Cell Mol. Physiol. 286: L1066-L1074, 2004). The ventilation gas (hypoxic) was return to normoxic gas, and the lungs were perfused with P3 (20 and 40 µM) in RPMI 1640 or RMPI 1640 for 10 min, after which the hypoxic challenge with 2% $O_2$ was repeated, and the PA pressure response was recorded.

Figure 6:
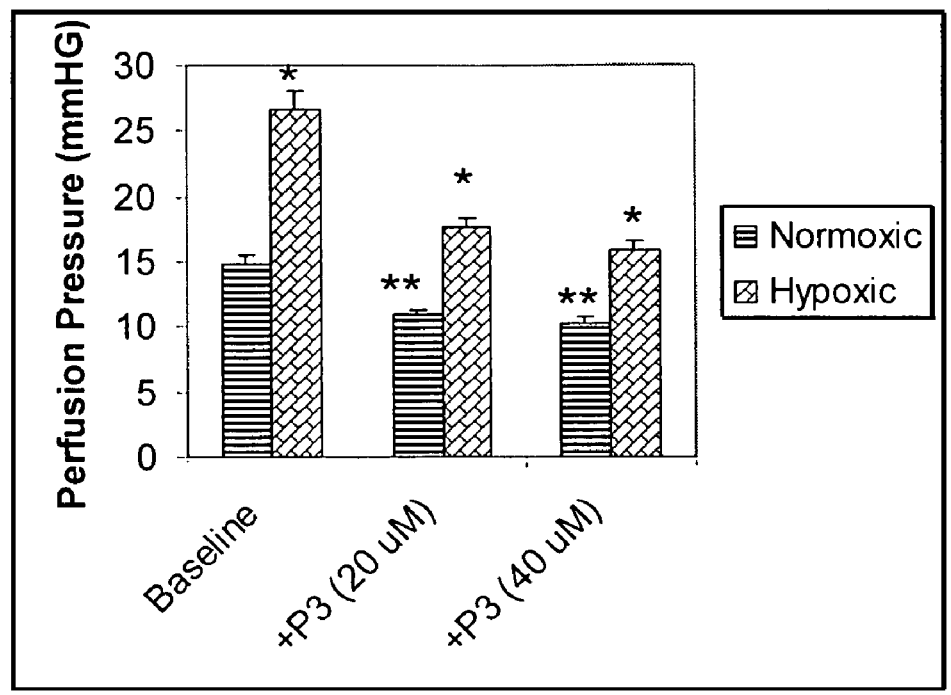
FIG. 6 shows the significant increase of hypoxia-induced vasoconstriction or pulmonary arterial pressure (PAP) compared to baseline PAP in normoxic lungs.

As shown in FIG. 6, significant increase of hypoxia-induced vasoconstriction or pulmonary arterial pressure (PAP) compared to baseline PAP in normoxic lungs. Infusion of 20 µM P3 significantly attenuated PAP in both normoxic and hypoxic lungs and was comparable to that observed with increased concentration (40 µM) of P3. In addition, the magnitude of P3-mediated reduction of PAP in hypoxic lung was much greater than in reduction in normoxic lungs.

Figure 7:
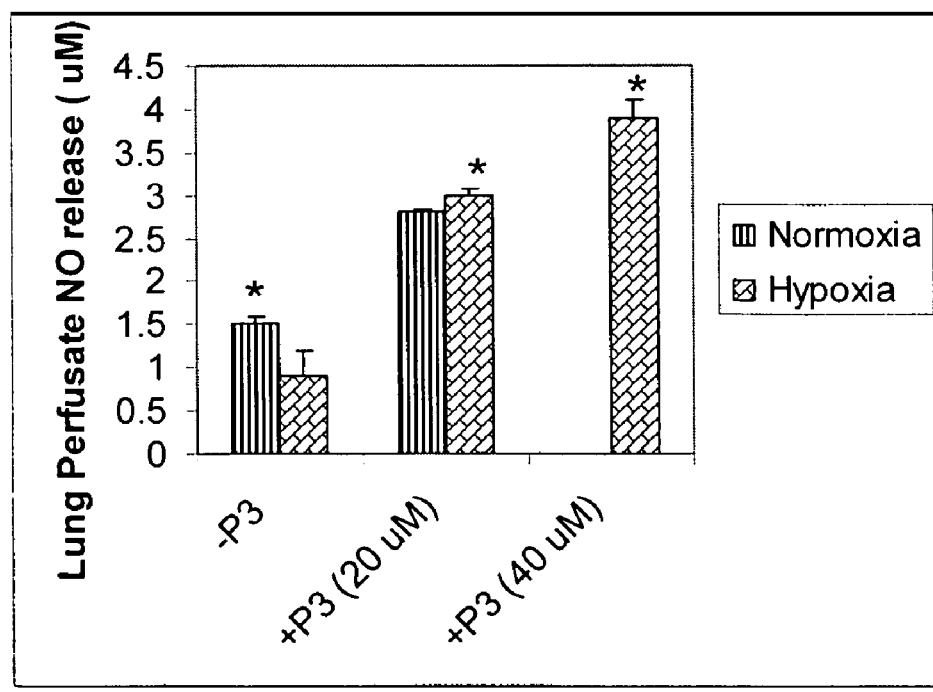
FIG. 7 shows that P3 increases NO release in perfusates from both the normoxic and hypoxic lungs.

The results in FIG. 7 show P3 increases NO release in perfusates from both the normoxic and hypoxic lungs.

EXAMPLE 5

In Vivo Vasodilation Effect of P3 in Hypoxic Lungs

Specific pathogen-free Sprague Dawley rats (200-250 g body weight) were exposed to hypoxia (10% inspired $O_2$) in a Coy Laboratory hypoxia chamber equipped with auto purge, airlock, and automated live animal filtration and dehumidification systems for 2 to 6 weeks. Control (normoxia) animals were maintained in similar humidity and temperature environment. Hypoxia exposure was 24 hr/day, except when the chamber was open twice a week for 10-15 min each to clean cages and replenish food and water. All rats were exposed to 12:12-hr light/dark cycle and allowed free access to standard rat food and water. Some rats were administered P3 (+P3) in saline (10 mg/kg or 20 mg/kg, ip) or saline alone (−P3) once every day starting 24 hr prior to initiation of exposure to hypoxia. After 2, 3, and 6 weeks exposure animals were use to measure various parameters including changes in pulmonary artery pressure, lung weight/body weight (LW/BW) ratio, and right vertical/heart weight (RV/HW) ratio.

Figure 8:
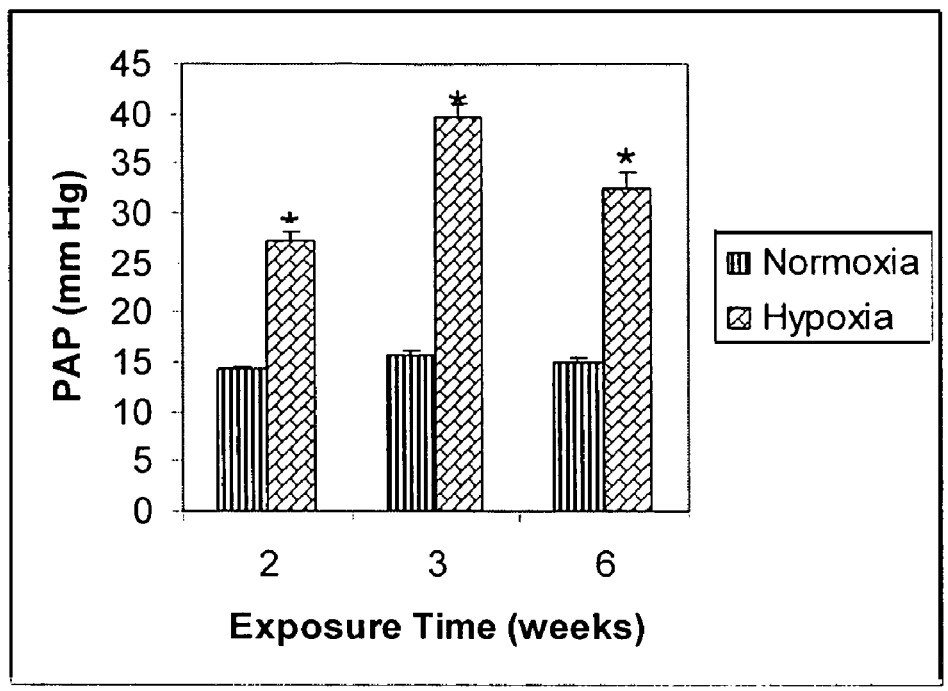
FIG. 8 shows that exposure to hypoxia for 2, 3, and 6 weeks caused significant increase in PAP compared to PAP in normoxic lungs
Figure 9:
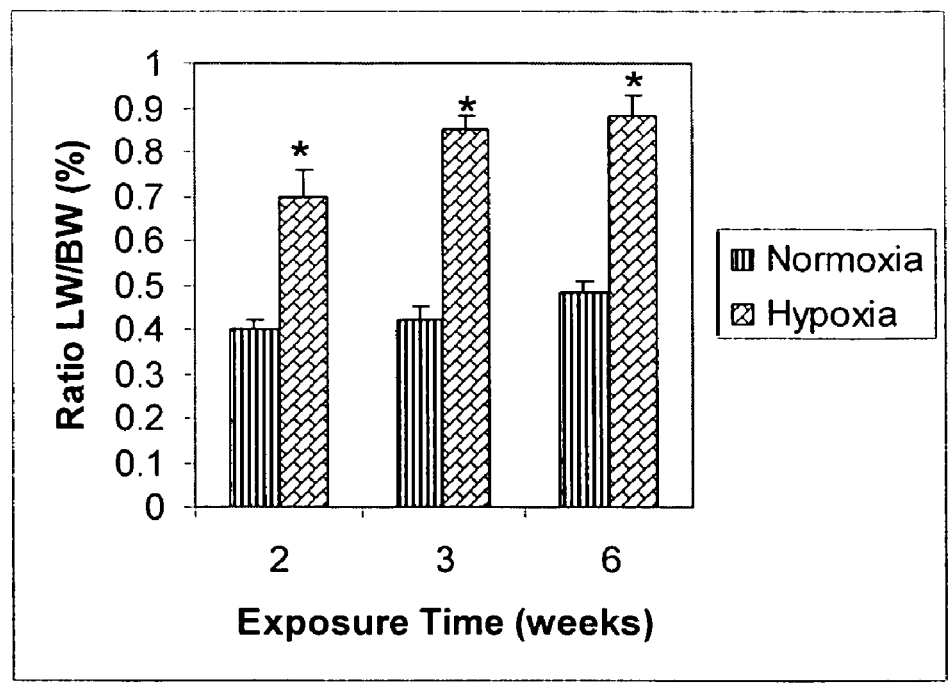
FIG. 9 shows increased LW/BW and RV/HW ratios due to hypoxia-induced lung and heart edema, respectively.
Figure 10:
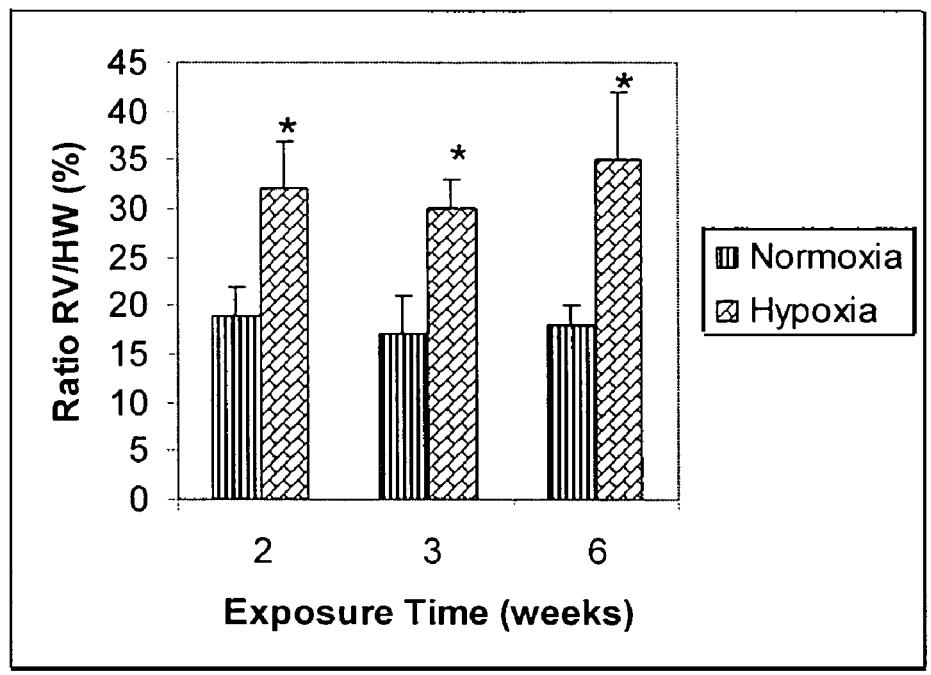
FIG. 10 shows increased LW/BW and RV/HW ratios due to hypoxia-induced lung and heart edema, respectively.
Figure 11:
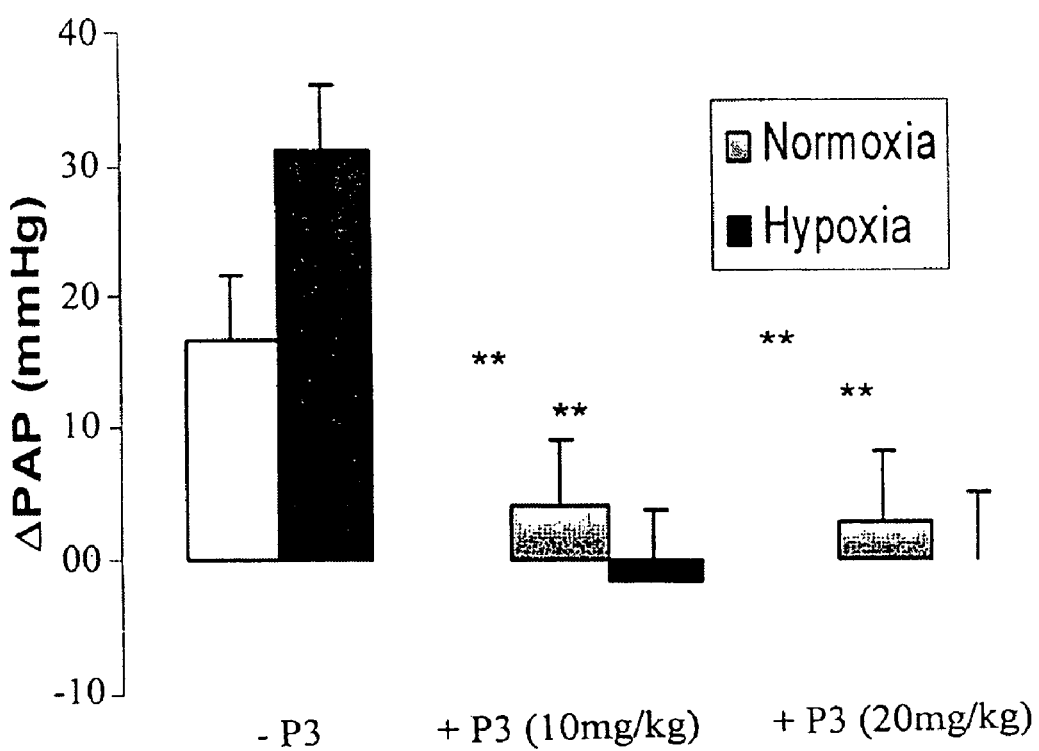
FIG. 11 shows hypoxia-induced PAP pressure attenuated by administration of P3.
Figure 12:
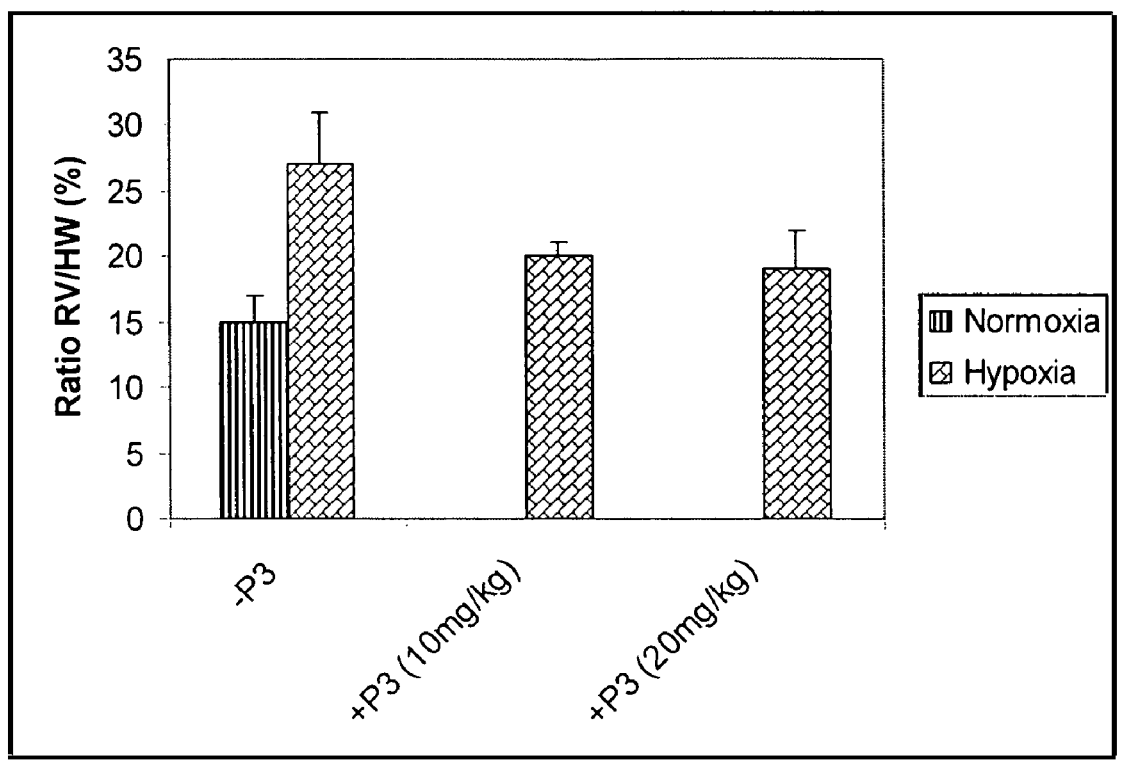
FIG. 12 shows hypoxia-induced RV/HW ratio attenuated by administration of P3.

As shown in FIG. 8, exposure to hypoxia for 2, 3, and 6 weeks caused significant increase in PAP compared to PAP in normoxic lungs. FIGS. 9 and 10 show increased LW/BW and RV/HW ratios due to hypoxia-induced lung and heart edema, respectively. Hypoxia-induced PAP pressure (FIG. 11) and RV/HW ratio (FIG. 12) were attenuated by administration of P3.

EXAMPLE 6

Treatment of Sexual Dysfunction

Sexual dysfunction (SD) is a significant clinical problem that can affect both males and females. The causes of SD may be both organic as well as psychological. Organic aspects of SD are typically caused by underlying vascular diseases. In the clinic, SD disorders have been divided into female sexual dysfunction (FSD) disorders and male sexual dysfunction (MSD) disorders. FSD is best defined as the difficulty or inability of a woman to find satisfaction in sexual expression. Male sexual dysfunction (MSD) is generally associated with erectile dysfunction, also known as male erectile dysfunction (MED). See, e.g., U.S. Pat. No. 6,878,529.

The compounds of the invention can be used for the treatment of sexual dysfunction in the male (e.g. male erectile dysfunction—MED) and in the female—female sexual dysfunction (FSD), e.g. female sexual arousal disorder (FSAD).

A. Female Sexual Dysfunction (FSD)

The categories of FSD are best defined by contrasting them to the phases of normal female sexual response: desire, arousal and orgasm. Arousal is the vascular response to sexual stimulation, an important component of which is genital engorgement and includes increased vaginal lubrication.

Hence, FSD occurs when a woman has an inadequate or unsatisfactory response in any of these phases. FSD categories include hypoactive sexual desire disorder, sexual arousal disorder, orgasmic disorders and sexual pain disorders. The peptides of the invention can be used to improve the genital response to sexual stimulation (as in female sexual arousal disorder) and, in doing so improve the associated pain, distress and discomfort associated with intercourse and so treat other female sexual disorders.

It has recently been hypothesized that there is a vascular basis for at least a proportion of patients with symptoms of FSAD. Thus, in accordance with one aspect of the invention, there is provided the use of the peptides of the subject invention for the treatment or prophylaxis of sexual arousal disorder, orgasmic disorder and sexual pain disorder, more preferably for the treatment or prophylaxis of sexual arousal disorder, orgasmic disorder, and sexual pain disorder, and most preferably in the treatment or prophylaxis of sexual arousal disorder. Drug candidates for treating FSAD, which are under investigation for efficacy, are primarily erectile dysfunction therapies that promote circulation to the male genitalia. They consist of two types of formulation, oral or sublingual medications (Apomorphine, Phentolamine, phosphodiesterase type 5 inhibitors e.g. Sildenafil), and prostaglandin that are injected or administered transurethrally in men, and topically to the genitalia in women. However, none of these therapies have yet been shown to be effective in the treatment of FSAD.

The peptides of the subject invention potentiate the endogenous vasorelaxant effects that occur during arousal. This leads to a prophylaxis and/or treatment of FSAD, such as through enhanced genital blood flow and thence genital engorgement.

B. Male Erectile Dysfunction (MED)

Male erectile dysfunction (MED) is defined as:

" . . . the inability to achieve and/or maintain a penile erection for satisfactory sexual performance (NIH Consensus Development Panel on Impotence, 1993) . . . "

It has been estimated that the prevalence of erectile dysfunction (ED) of all degrees (minimal, moderate and complete impotence) is 52% in men 40 to 70 years old, with higher rates in those older than 70. The condition has a significant negative impact on the quality of life of the patient and their partner, often resulting in increased anxiety and tension which leads to depression and low self esteem. Whereas two decades ago, MED was primarily considered to be a psychological disorder, it is now known that for the majority of patients there is an underlying organic cause.

Penile erection is a haemodynamic event which is dependent upon the balance of contraction and relaxation of the corpus cavernosal smooth muscle and vasculature of the penis (Lerner et al 1993). Relaxation of the corpus cavernosal smooth muscle leads to an increased blood flow into the trabecular spaces of the corpus cavernosa, causing them to expand against the surrounding tunica and compress the draining veins. This produces a vast elevation in blood pressure which results in an erection (Naylor, 1998).

During sexual arousal in the male, NO is released and the endothelium and binds to and activates soluble guanylate cyclase (sGC) located in the smooth muscle cells and endothelium, leading to an elevation in intracellular cyclic guanosine 3',5'-monophosphate (cGMP) levels.

Sildenafil citrate (also known as Viagra®) has recently been developed by Pfizer as the first oral drug treatment for MED. Sildenafil acts by inhibiting cGMP breakdown in the corpus cavemosa by selectively inhibiting phosphodiesterase 5 (PDE5), thereby limiting the hydrolysis of cGMP to 5'GMP (Boolel et al., 1996; Jeremy et al., 1997) and thereby increasing the intracellular concentrations of cGMP and facilitating corpus cavemosal smooth muscle relaxation.

The present invention is advantageous as it provides a means for restoring a normal sexual arousal response—namely increased penile blood flow leading to erection of the penis in males and an increased genital engorgement in females. Hence, the present invention provides a means to restore, or potentiate, the normal sexual arousal response.

EXAMPLE 7

Treatment of Cerebral Ischemia

Patients experiencing cerebral ischemia often suffer from disabilities ranging from transient neurological deficit to irreversible damage (stroke) or death. Cerebral ischemia, i.e., reduction or cessation of blood flow to the central nervous system, can be characterized as either global or focal.

Focal cerebral ischemia refers to cessation or reduction of blood flow within the cerebral vasculature resulting from a partial or complete occlusion in the intracranial or extracranial cerebral arteries. Such occlusion typically results in stroke, a syndrome characterized by the acute onset of a neurological deficit that persists for at least 24 hours, reflecting focal involvement of the central nervous system and is the result of a disturbance of the cerebral circulation. Other causes of focal cerebral ischemia include vasospasm due to subarachnoid hemorrhage or iatrogenic intervention.

Global cerebral ischemia refers to reduction of blood flow within the cerebral vasculature resulting from systemic circulatory failure. The failure of the circulatory system to maintain adequate cellular perfusion leads to a reduction of oxygen and nutrients to tissues. Thus, global cerebral ischemia results from severe depression of cardiac performance. Further causes include interventional procedures, such as carotid angioplasty, stenting or endarterectomy, which might otherwise result in focal cerebral ischemia, and also cardiac procedures which may result in global cerebral ischemia, such as cardiac catheterization, electrophysiologic studies, and angioplasty.

Those skilled in the art are easily able to identify patients having a stroke or at risk of having a stroke, cerebral ischemia, head trauma, or epilepsy. For example, patients who are at risk of having a stroke include, but are not limited to, patients having hypertension or undergoing major surgery.

Traditionally, emergent management of acute ischemic stroke consists of mainly general supportive care, e.g. hydration, monitoring neurological status, blood pressure control, and/or anti-platelet or anti-coagulation therapy. Heparin has been administered to stroke patients with limited and inconsistent effectiveness. Treatment with systemic t-PA is associated with increased risk of intracerebral hemorrhage and other hemorrhagic complications. Aside from the administration of thrombolytic agents and heparin, there are no therapeutic options currently on the market for patients suffering from occlusion focal cerebral ischemia. See, e.g., U.S. Pat. No. 6,858,383.

In one embodiment, the peptides of the subject invention can be used to treat ischemia.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A method for regulating cGMP and/or cAMP levels wherein said method comprises administering, to a subject in need of such regulation, a peptide selected from the group consisting of P3 (SEQ ID NO: 1) and, P4 (SEQ ID NO: 2).

2. The method, according to claim 1, wherein said peptide is administered with a pharmaceutically acceptable carrier.

3. The method, according to claim 1, wherein said peptide is administered via a route selected from the group consisting of oral, intraperotoneal, pulmonary, intramuscular, subcutaneous, intraarterial, intravenous, intrathecal injection and catheterization.

4. The method, according to claim 1, wherein the subject is a human.

5. The method, according to claim 3, wherein said peptide is administered with a pharmaceutically acceptable carrier.

6. The method, according to claim 3, wherein the subject is a human.

* * * * *

UNITED STATES PATENT AND TRADEMARK OFFICE
CERTIFICATE OF CORRECTION

PATENT NO. : 7,476,655 B2  Page 1 of 1
APPLICATION NO. : 11/433113
DATED : January 13, 2009
INVENTOR(S) : Jawaharlal M. Patel It is certified that error appears in the above-identified patent and that said Letters Patent is hereby corrected as shown below:

Column 1,
Line 18 "the government may have certain" should read --the government has certain--.

Column 2,
Line 58 "tyrosinee" should read --tyrosine--.

Column 14,
Line 54 "74 % N2" should read --74% $N_2$--.
Line 64 "74 % N2" should read --74% $N_2$--.

Column 17,
Line 11 "corpus cavemosa" should read --corpus cavernosa--.
Line 15 "corpus cavemosal" should read --corpus cavernosa--.

Signed and Sealed this

Thirty-first Day of March, 2009

JOHN DOLL
*Acting Director of the United States Patent and Trademark Office*